United States Patent [19]

Hurd

[11] Patent Number: 4,925,293
[45] Date of Patent: May 15, 1990

[54] INTRAOCULAR BIOMETER FOR A SLIT LAMP

[76] Inventor: William C. Hurd, 1271 E. Parkway S., Memphis, Tenn. 38114

[21] Appl. No.: 657,873

[22] Filed: Oct. 4, 1984

[51] Int. Cl.⁵ .............................................. A61B 3/10
[52] U.S. Cl. .................................... 351/214; 351/212
[58] Field of Search ........................ 351/205, 212, 214

[56] References Cited

U.S. PATENT DOCUMENTS

| | | | |
|---|---|---|---|
| 3,888,569 | 6/1975 | Munnerlyn et al. | 351/214 |
| 4,019,813 | 4/1977 | Cornsweet et al. | 351/214 |
| 4,398,812 | 8/1983 | Kelman | 351/214 |

FOREIGN PATENT DOCUMENTS

| | | |
|---|---|---|
| 2520445 | 11/1975 | Fed. Rep. of Germany . |
| 2641004 | 3/1978 | Fed. Rep. of Germany . |

Primary Examiner—P. M. Dzierzynski
Attorney, Agent, or Firm—Staas & Halsey

[57] ABSTRACT

The present invention relates to an apparatus which attaches to a conventional slit lamp instrument and measures any portion of an eye which can be visualized using the slit lamp instrument. The apparatus includes a device for detecting movement of the slit lamp instrument, a calculating device which calculates distances measured in the eye in dependence upon the movement of the slit lamp instrument, and an output device for outputting the distance measured.

11 Claims, 4 Drawing Sheets

INTRAOCULAR BIOMETER FOR A SLIT LAMP

BACKGROUND OF THE INVENTION

This invention relates to an apparatus which attaches to a slit lamp and provides accurate measurements of an eye. Measurements which are made include the thickness of the cornea, pupil size, the diameter of the anterior chamber, anterior chamber depth, anterior-posterior diameter and optic disc cup diameter.

Slit lamps are routinely used by ophthalmologists and optometrists to biomicroscopically examine the eye of a patient. There are no devices of which the inventor is aware for accurately measuring those parts of the eye visualized by the slit lamp. Prior art devices which make some measurements of the eye include those disclosed in the West German Offenlegungsschrift No. 2,520,445; U.S. Pat. No. 4,398,812 to Kelman; and U.S. Pat. No. 4,019,813 to Cornsweet et al.

The device described in the West German Offenlegungsschrift No. 2,520,445 consists of a microscope, keratometer and a slit lamp. The only measurement this device is capable of making is the thickness of the cornea.

The device described in the patent to Kelman measures the diameter of the anterior chamber of the eye by using two sources of light and a calibrated scale. In other words, this device is a separate unit which is not used in conjunction with a slit lamp and therefore is relatively expensive while being capable of making only a single measurement.

The device described in the patent to Cornsweet et al. is a very sophisticated instrument which uses a television camera for measuring various portions of the eye such as the thickness of the cornea, the depth of the anterior chamber, the thickness of the lens and the transparency of different portions of the eye.

In addition, ultrasonic measuring devices are presently used to measure the anterior-posterior diameter of an eye to calculate the power of magnification required for an intraocular lens implant. Such ultrasonic measuring devices are more expensive and less available than slit lamps and in addition, the effects of ultrasonic radiation on the human body are not all known. Slit lamps on the other hand, have long been in use without harm since they use light which the eye is designed to receive.

The devices described above illustrate the types of devices currently available to an eye physician. The devices are either extremely limited in their capabilities, such as those described in the West German Offenlegungsschrift and the patent to Kelman, or the device is so very expensive that the ordinary practitioner cannot possibly afford to own such a device, like the one patented by Cornsweet et al.

SUMMARY OF THE INVENTION

An object of the present invention is to overcome the limitations of the prior art by providing an add-on unit for existing slit lamps which is relatively inexpensive and which is capable of making many measurements of the interior of an eye.

Another object of the present invention is to provide a device, mountable on a slit lamp, for measuring the thickness of the cornea of an eye.

Yet another object of the present invention is to provide a device, mountable on a slit lamp, for measuring the diameter of the anterior chamber of an eye.

Still another object of the present invention is to provide a device, mountable on a slit lamp, for measuring the anterior-posterior diameter of an eye.

A further object of the present invention is to monitor the cup/disc ratio in glaucoma patients, using a slit lamp attachment.

A still further object of the present invention is to monitor the growth of a choroidal tumor using a slit lamp attachment.

A yet further object of the present invention is to provide the measurements necessary to determine the size and power of an intraocular lens using inexpensive equipment.

The above objects are obtained by providing a device which includes input means, such as three variable resistors, attachable to a slit lamp to detect movement along each of three axes of movement of the slit lamp; a calculating device for calculating a distance based on beginning and ending points of a measurement by using a previously stored formula relating the values of the resistors to the distance measured for each part of the eye which can be measured; and an output device for outputting the distance measured.

The above objects, together with other objects and advantages which will be subsequently apparent, reside in the details of the construction and operation as more fully hereinafter described and claimed, reference being had to the accompanying drawings forming a part hereof, wherein like numerals refer to like parts throughout.

DESCRIPTION OF THE PREFERRED EMBODIMENT

Figure 1A:
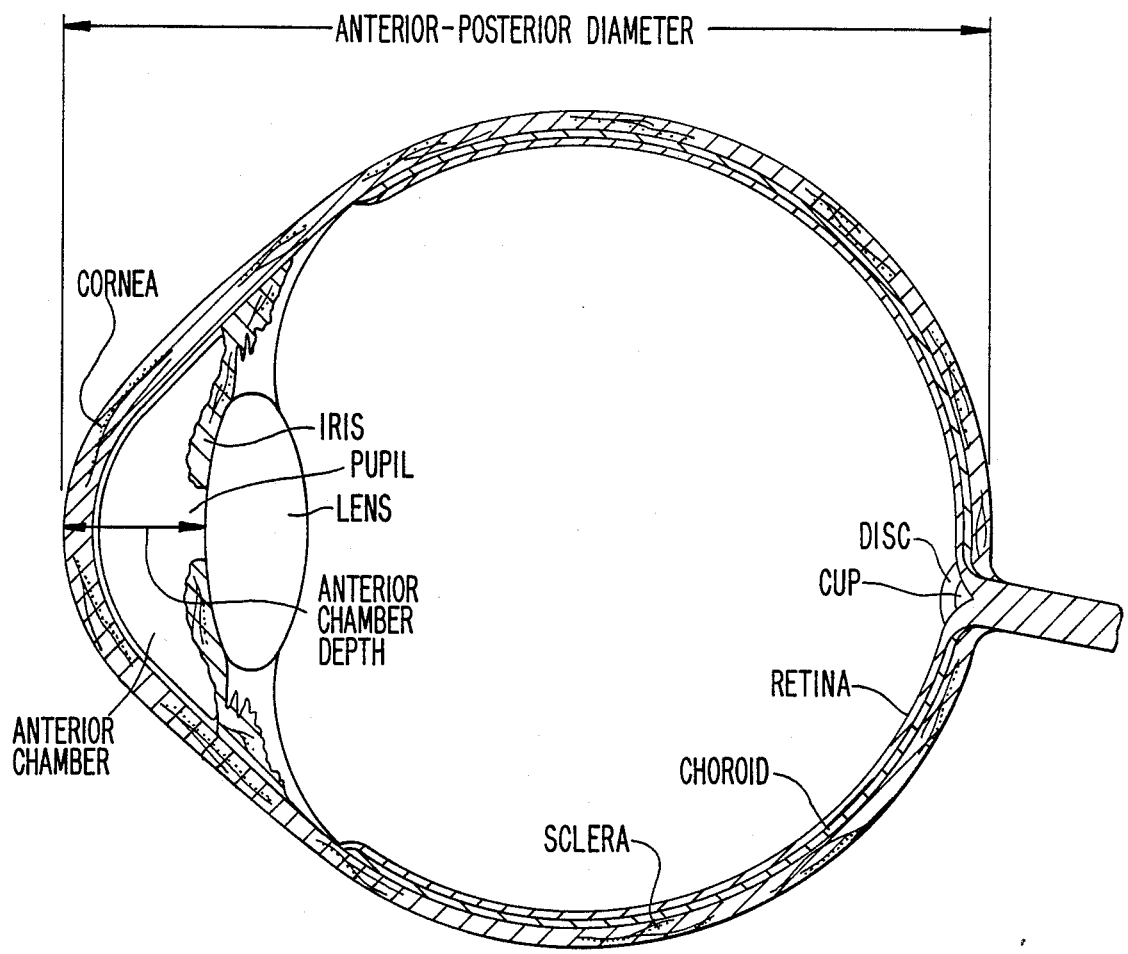
FIG. 1A is an illustration of a human eye in axial cross-section.
Figure 1B:
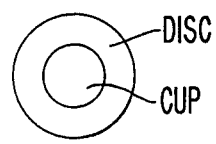
FIG. 1B is an illustration of the optic cup and optic disc of an eye as viewed through the pupil.
Figure 2:
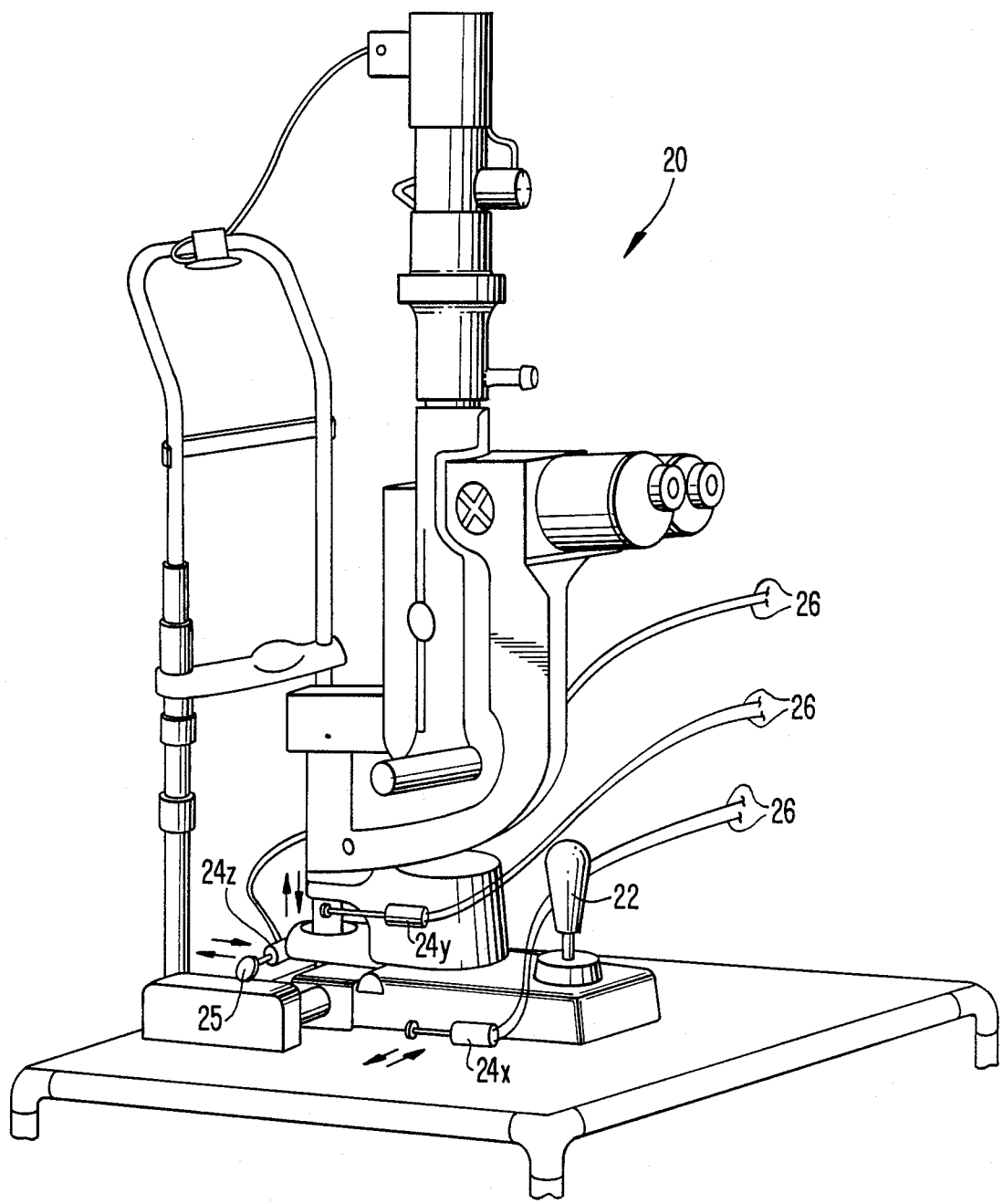
FIG. 2 is an illustration of a slit lamp with the variable resistors of the present invention mounted thereon.

An apparatus according to the present invention measures any part of the eye that can be visualized using a slit lamp, such as the slit lamp instrument 20 illustrated in FIG. 2, by detecting the movement of the slit lamp instrument 20 controlled by a joystick 22 conventionally provided on slit lamp instruments. The movements controlled by the joystick 22 are detected by variable resistors 24 connected to wheels 25 which contact the slit lamp instrument 20 via gear teeth or other secure means. The variable resistors 24 are mounted on the slit lamp instrument 20 such that each movement of the instrument 20 causes a change in the resistance of at least one of the variable resistors 24. In FIG. 2, variable resistor 24$x$ detects left-right movement, variable resistor 24$y$ detects up-down movement, and variable resistor 24$z$ detects movement toward and away from the patient. Each of the variable resistors 24 is connected to a pair of input leads 26 which carry a current passing through the resistors 24.

Figure 3:
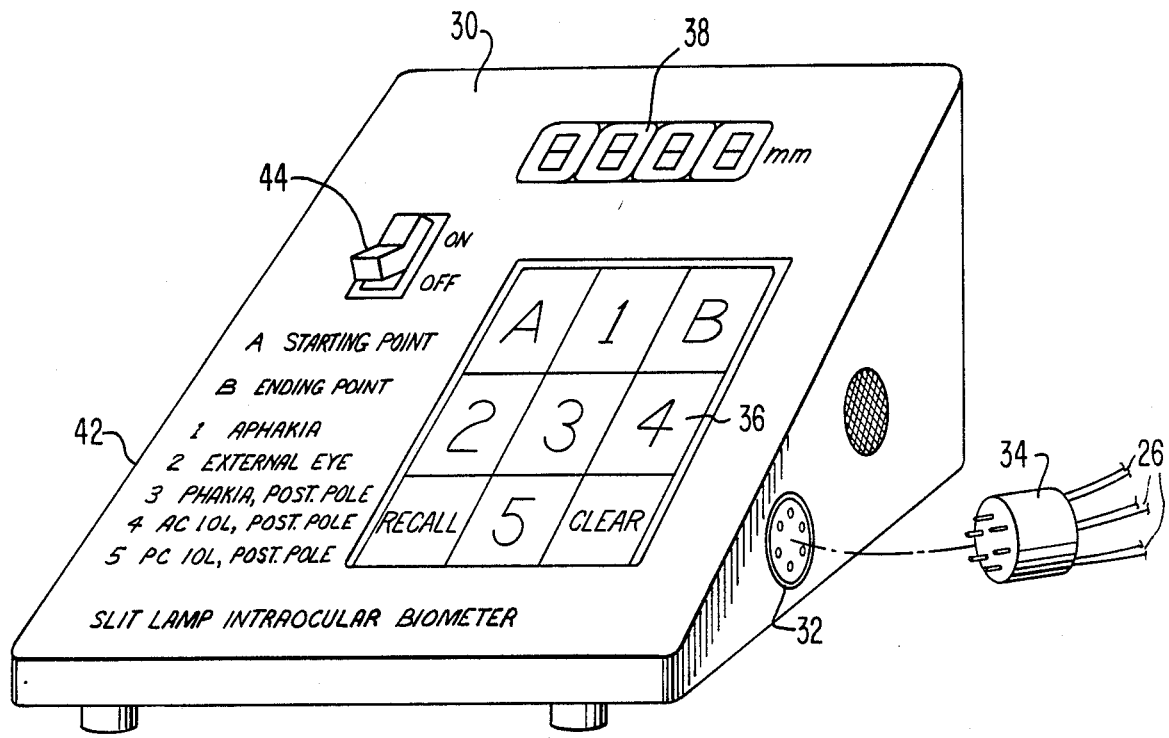
FIG. 3 is an illustration of a control device cabinet with an input panel and an output display unit according to the present invention.

A control device cabinet 30 is illustrated in FIG. 3. The control device cabinet 30 includes a six prong female connector 32 which connects the cabinet 30 to the input leads 26 via a six prong male connector 34. An input panel 36 is used by an eye examiner to indicate beginning and ending points of measurement and the type of measurement being made. The measurement is indicated on a digital output display 38 or an audio output 40 such as a minispeaker. Brief instructions 42 for the input panel appear on the face of the control device cabinet 30 and a lighted power switch 44 provides power to the devices in the control device cabinet 30 and to the variable resistors 24 via the six prong connectors 32 and 34 and the input leads 26.

Figure 4:
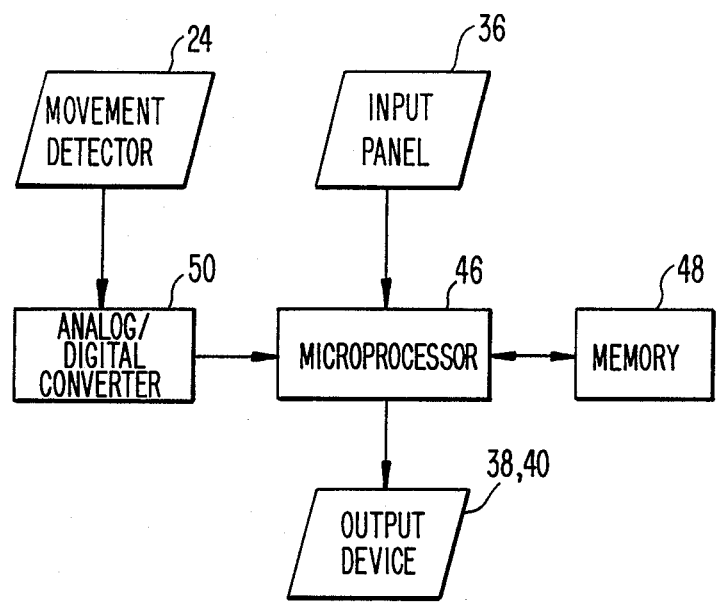
FIG. 4 is a block diagram of the components of an embodiment of the present invention.

Inside the control device cabinet 30 is a calculating device illustrated in FIG. 4 as including a microprocessor 46 and a memory 48. As the resistances of the variable resistors 24 change due to movement of the slit lamp instrument 20, the calculating device measures the resistances in ohms. The microprocessor 46 then calculates the distance between the beginning and ending points using a formula stored in the memory 48.

According to tests performed using a prototype intraocular biometer, the formula stored in the memory 48 is not dependent upon the type of lens used with the slit lamp or the condition of the patient's eye. Instead, only the relationship between the variable resistor's adjustment control and the resistance provided by the variable resistors needs to be considered in developing the formula. Tests have been conducted using a prototype intraocular biometer in which the slit lamp moved the same distance under varying optical conditions.

Therefore, the selection of resistors and the connection of the resistors to the slit lamp are critical to the production of an accurate intraocular biometer according to the present invention. What is required is a variable resistor which is sensitive to small movements of the slit lamp and has a linear relationship between the distance moved and the resistance provided by the resistor. For example, four Radio Shack Alpha B-type variable resistors with a five centimeter rotating shaft were tested to determine their suitability for use in the intraocular biometer. The maximum resistances provided by the resistors was 10 kilohms, 500 kilohms, 1 megohm and 2 megohms, respectively. The resistances provided by each of these resistors were measured with 10 degree increments in rotation of the shaft of the variable resistors with the results indicated in the table in Appendix A.

From the data in the table in Appendix A, it is apparent that a generally linear relationship between degree of rotation and resistance occurs between 100 and 250 degrees. Exceptions to this are found in the 500 kilohm resistor which has a linear range between 90 and 210 degrees, and the two megohm resistor which has two linear ranges between 90 and 170 degrees, and 180 and 260 degrees. The resistor with the longest linear range, between 100 and 250 degrees, with a small deviation in change of resistance is the one megohm resistor which has an average (mean) change in resistance of 46.7 kilohms per ten degrees (4.67 kilohms per degree) with a maximum change of 51 kilohms and a minimum change of 43 kilohms per ten degrees. Of the resistors tested, the one megohm resistor is therefore best suited for use in the intraocular biometer and will be used below as an illustration of how to derive the formula which is stored in the memory 48. Presumably, considerably more accurate and sensitive resistors are readily available which would have a deviation of one percent or less instead of the approximately ten percent variance of the one megohm resistor tested.

Figure 5:
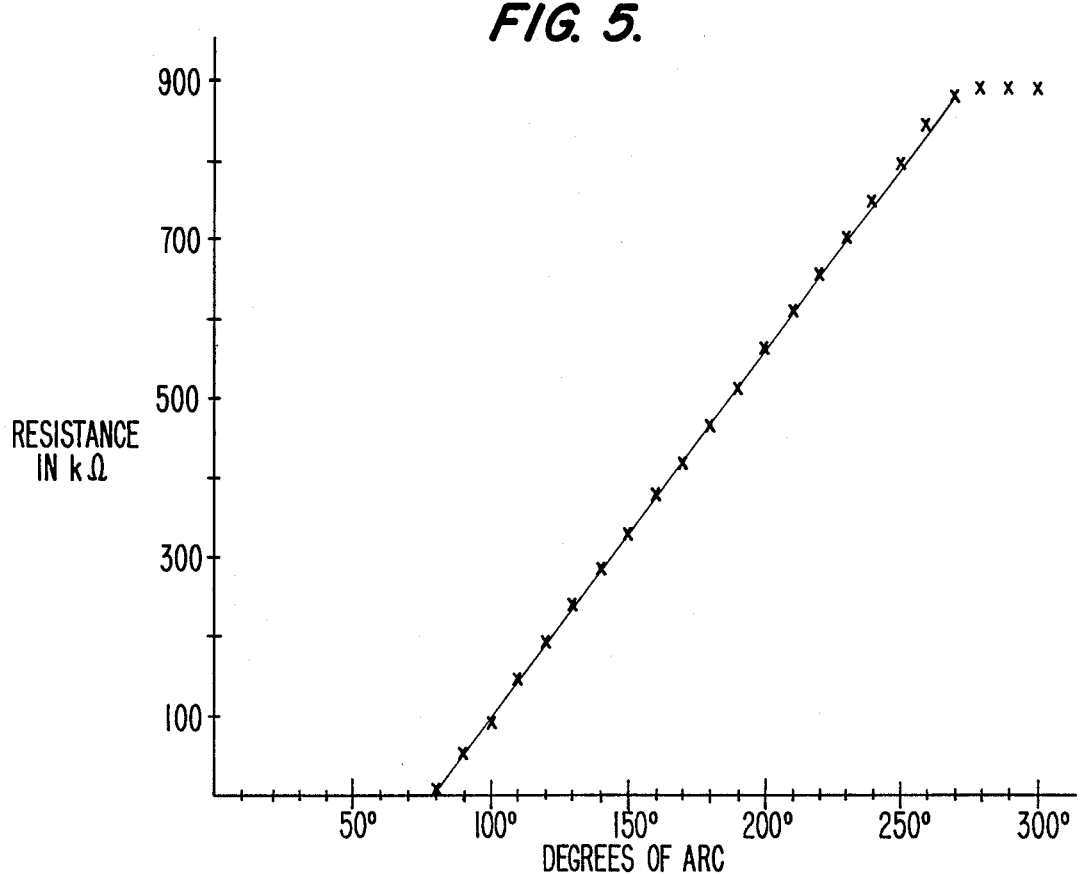
FIG. 5 is a graph of resistance vs. distance used in developing a formula relating resistance to distances in an eye.

The data in the table in Appendix A for the one megohm resistor is plotted in FIG. 5 which clearly shows the linear range between 100 and 250 degrees. A formula for a line which is a good approximation of the relationship between resistance and rotation can be found using regression techniques such as least-squares; however a simple average of the change between 100 and 250 degrees will be used in this example for simplicity. As stated above, the average change between 100 and 250 degrees is 4.67 kilohms per degree. The following formula (1) gives the relationship between degrees of rotation and resistance, where DR is degrees of rotation, R is resistance in kilohms and I is the x-axis intercept of the line in FIG. 5 relating resistance and degrees of rotation.

$$DR = (1/4.67)R + I \tag{1}$$

By inserting the values in the above table for 220°, the value of I is found to be 80 as indicated below in formulas (2) and (3).

$$220 = (0.214)(654) + I \tag{2}$$

$$I = 220 - 140 = 80 \tag{3}$$

In FIG. 2, small wheels 25 are illustrated as attached to the shafts of the variable resistors 24 and making contact with portions of the slit lamp instrument 20. Movement of the slit lamp instrument 20 is translated into rotation of the rotating shaft of the variable resistors by movement of the wheels 25. The size of the wheels 25 determines how much the rotating shaft moves for a given amount of movement of the slit lamp instrument 20. Selecting the size of the wheels 25 to be as small as possible and still permit all parts of the eye to be measured within the linear range of the resistor maximizes the sensitivity of the biometer, because a small wheel will cause registrable changes in the variable resistor for smaller movements of the slit lamp instrument 20 than will a large wheel.

Assuming that the largest measurement needed to be made is approximately 1.5 inches, formulas (4) and (5) below show that a wheel with a radius of approximately 15 mm will permit measurements of the eye over the 150° linear range of the 1 megohm resistor.

$$1.5'' = (150/360)(2\pi r) \tag{4}$$

$$r = (1.5)/[(150/180)(3.14159)] = 0.573'' < 15 \text{ mm} \tag{5}$$

According to equation (6) below, one degree of rotation of a 15 mm wheel is approximately a 0.26 mm movement of the slit lamp instrument 20.

$$(1/360)(2\pi r) = (3.14159/180)(15 \text{ mm}) = 0.262 \text{ mm} \tag{6}$$

Using the values in equations (2) and (6), equation (1) becomes equations (7) and (8) which relate resistance R to distance D for the one megohm resistor with a 15 mm wheel.

$$(0.262)DR = (0.262)(0.214)R + (0.262)(80) \tag{7}$$

$$D = 0.056R + 21 \tag{8}$$

The accuracy of the intraocular biometer can be illustrated using the 15 mm wheel on the one megohm resistor, which presumably can be replaced by a much more accurate resistor, for the following sample measurement. Using a starting point of 150 degrees of rotation which corresponds to 39.3 mm and an ending point of 200 degrees of rotation which corresponds to 52.4 mm, the distance measured equals 13.1 mm. Using formula (8) above, the corresponding resistance of 324 kilohms at 150 degrees of rotation is converted by the formula to 39.144 mm, while 563 kilohms at 200 degrees of rotation is converted by the formula to 52.528 mm or a difference of 13.384 mm for an error of approximately 0.28 mm. This is an error of only 2 percent. However, as mentioned above, more accurate resistors with a smaller deviation, i.e., a more linear range, are presumably available. In addition, resistors with a larger linear range may be available which could be used with smaller wheels to both decrease the error and increase the sensitivity of the biometer. In addition, the equation used was a very rough approximation and more accurate regression techniques can be used to reduce the error further.

The example above relates to a measurement along one of the axes of movement, such as the anterior-posterior diameter. However it should be easily understood that two and three dimensional measurements are possible by measuring the distance moved along each of the axes in the manner described above and then combining these measurements to find the two-dimensional or three-dimensional distance actually moved. As described above, the optical conditions, i.e., the presence or absence of the lens in the eye and the type of lenses used with the slit lamp 20, do not need to be included in the calculations according to tests which have been performed on a prototype intraocular biometer.

Referring to FIG. 4, an eye examiner, e.g., an ophthalmologist or an optometrist, uses the intraocular biometer in the following manner. First, the eye examiner positions the slit lamp instrument 20 so that a beginning point of a measurement is illuminated by the slit lamp 20. Then the eye examiner presses the A key on the input panel 36 (FIG. 3) which causes the resistance values of the variable resistors 24 to be converted by an analog/digital converter 50 and to be used as input in calculations performed by the microprocessor 46 using the formula stored in the memory 48. The result of this calculation is then stored in the memory 48. Next, the eye examiner positions the slit lamp instrument 20 so that the end point of the measurement is illuminated by the slit lamp 20. When the B key on the input panel 36 is depressed by the eye examiner, the resistance values are again used as input to the formula for the measurement and the difference between these values is displayed on the output display 38 or output as an audio signal by the minispeaker 40.

The intraocular biometer adds a new dimension to eye examination by providing measurement of any portion of the eye which can be visualized by using a slit lamp instrument. A Hruby or Goldmann lens may be used with the intraocular biometer to provide a more detailed view of the posterior pole of the eye without affecting the measurement. The measurements provided by the intraocular biometer make it possible for any eye examiner to accurately measure the cup/disc ratio in glaucoma patients and to monitor the size of a choroidal tumor. In addition, by measuring the anterior-posterior diameter of the eye, the power of an intraocular lens, implanted after extraction of cataracts, can be calculated. At present, the anterior-posterior diameter is measured by expensive ultrasound devices.

The many features and advantages of the present invention are apparent from the detailed specification, and thus it is intended by the appended claims to cover all such features and advantages of the apparatus which fall within the true spirit and scope of the invention. Further, since numerous modifications and changes will readily occur to those skilled in the art, it is not desired to limit the invention to the exact construction and operation illustrated and described. Accordingly, all suitable modifications and equivalents may be resorted to, falling within the scope and spirit of the invention.

APPENDIX A
TABLE

| degrees | 2M kΩ | 1M kΩ | 500k kΩ | 10k kΩ |
|---|---|---|---|---|
| 10 | 0 | 0 | 0 | 0 |
| 20 | 0 | 0 | 0 | 0 |
| 30 | 0 | 0 | 0 | 0 |
| 40 | 0 | 0 | 0 | 0 |
| 50 | 0 | 0 | 0 | 0 |
| 60 | 0 | 0 | 0 | 0 |
| 70 | 0 | 0 | 0 | 0 |
| 80 | 2 | 6 | 1 | 0 |
| 90 | 82 | 56 | 6 | .6 |
| 100 | 183 | 97 | 13 | 1.2 |
| 110 | 273 | 145 | 18 | 1.9 |
| 120 | 372 | 193 | 23 | 2.4 |
| 130 | 475 | 236 | 29 | 3.1 |
| 140 | 570 | 281 | 34 | 3.4 |
| 150 | 663 | 324 | 39 | 3.7 |
| 160 | 766 | 375 | 44 | 4.3 |
| 170 | 861 | 420 | 49 | 4.9 |
| 180 | 939 | 463 | 53 | 5.5 |
| 190 | 1048 | 512 | 60 | 6.2 |
| 200 | 1148 | 563 | 65 | 6.9 |
| 210 | 1241 | 610 | 72 | 7.5 |
| 220 | 1348 | 654 | 86 | 8.1 |
| 230 | 1440 | 700 | 168 | 8.7 |
| 240 | 1541 | 746 | 240 | 9.2 |
| 250 | 1641 | 798 | 318 | 9.8 |
| 260 | 1730 | 841 | 374 | 9.8 |
| 270 | 1743 | 874 | 418 | 9.8 |
| 280 | 1743 | 877 | 421 | 9.8 |
| 290 | 1743 | 877 | 421 | 9.8 |
| 300 | 1743 | 877 | 421 | 9.8 |
| 310 | 1743 | 877 | 421 | 9.8 |

What is claimed is:
1. An intraocular biometer, mountable on a slit lamp used to examine an eye, said intraocular biometer comprising:
   input means for detecting movement of the slit lamp;
   calculating means, operatively connected to said input means, for calculating a distance measured in the eye in dependence upon the movement of the slit lamp; and
   output means, operatively connected to said calculating means, for outputting the distance measured.
2. An intraocular biometer as recited in claim 1, wherein said input means comprises movement detecting means mechanically linked to the slit lamp and operatively connected to said calculating means, for detecting the movement of the slit lamp.
3. An intraocular biometer as recited in claim 2, wherein the slit lamp has axes of movement, and
   wherein said movement detecting means comprises variable resistors, operatively connected to said calculating means, each of said variable resistors mechanically linked to the slit lamp to detect the movement of the slit lamp along one of the axes of movement.

4. An intraocular biometer as recited in claim 1, further comprising an input panel, operatively connected to said calculating means, for selecting a formula for calculating the distance measured and for indicating beginning and ending points of the distance measured.

5. An intraocular biometer as recited in claim 1, wherein said calculating means comprises:
   a microprocessor, operatively connected to said input means and said output means, for calculating the distance measured; and
   a memory, operatively connected to said microprocessor, for storing a formula for converting the movement of the slit lamp into the distance measured in the eye.

6. An intraocular biometer as recited in claim 5,
   wherein the slit lamp has axes of movement and said input means comprises variable resistors having a resistance which is variable, operatively connected to said calculating means, each of said variable resistors mechanically linked to the slit lamp to detect the movement of the slit lamp along one of the axes of movement, and
   wherein said calculating means further comprises an analog/digital converter, operatively connected to said variable resistors and said microprocessor, for converting the resistance of said variable resistors into digital values.

7. An intraocular biometer as recited in claim 1, further comprising a joystick, coupled to the slit lamp, for moving the slit lamp.

8. A measuring device for measuring a remote area, comprising:
   light providing means for providing a single spot of light in the remote area to be measured, the single spot of light being movable around the remote area by adjustment of said light providing means;
   input means, coupled to said light providing means, for detecting the adjustment of said light providing means;
   calculating means, operatively connected to said input means, for calculating a distance measured in the remote area in dependence upon the adjustment of said light providing means; and
   output means, operatively connected to said calculating means, for outputting the distance measured.

9. A method for measuring a distance in a remote area using a light supplying device, comprising the steps of:
   (a) illuminating a first point in the remote area with a single beam of light from the light supplying device;
   (b) moving the light supplying device by an amount of movement to illuminate a second point in the remote area with the single beam of light; and
   (c) calculating the distance between the first point and the second point from the amount of movement of the light supplying device.

10. A method for measuring a distance in a remote area as recited in claim 9, wherein step (c) comprises the steps of:
   (i) detecting the amount of movement of the light supplying device using a variable resistor;
   (ii) recording a first resistance value when the first point is illuminated;
   (iii) recording a second resistance value when the second point is illuminated; and
   (iv) converting the first and second resistance values into first and second positions, respectively, and calculating the distance between the first and second positions.

11. A method for measuring a distance in a remote area as recited in claim 9, wherein steps (a) and (b) each comprises maneuvering a joystick coupled to the light supplying device to illuminate the first and second points, respectively.

* * * * *